(12) United States Patent
Wolter et al.

(10) Patent No.: US 6,794,527 B1
(45) Date of Patent: Sep. 21, 2004

(54) HYDROLYZABLE AND POLYMERIZABLE SILANES

(75) Inventors: Herbert Wolter, Tauberbischofsheim (DE); Siegfried Schmitzer, Wuerzburg (DE)

(73) Assignee: Fraunhofer-Gesellschaft zur Foerderung der Angewandten Forschung E.V., Munich (DE)

( * ) Notice: Subject to any disclaimer, the term of this patent is extended or adjusted under 35 U.S.C. 154(b) by 95 days.

(21) Appl. No.: 09/936,206

(22) PCT Filed: Jul. 3, 2000

(86) PCT No.: PCT/DE00/00765

§ 371 (c)(1),
(2), (4) Date: Dec. 13, 2001

(87) PCT Pub. No.: WO00/53612

PCT Pub. Date: Sep. 14, 2000

(30) Foreign Application Priority Data

Mar. 11, 1999 (DE) .......................... 199 10 895

(51) Int. Cl.[7] .............. C07F 7/12; C07F 7/10; C07F 7/18; C07G 77/20; C07G 77/22
(52) U.S. Cl. ...................................... 556/419
(58) Field of Search ........................ 556/419

(56) References Cited

U.S. PATENT DOCUMENTS

| | | | |
|---|---|---|---|
| 3,773,607 A | 11/1973 | Marzocchi | 161/176 |
| 5,332,429 A | 7/1994 | Mitra et al. | 106/35 |
| 5,348,771 A | 9/1994 | Lee et al. | 427/515 |
| 5,414,093 A | 5/1995 | Wolter | 549/214 |
| 5,674,965 A | 10/1997 | Carey et al. | 528/27 |
| 5,717,125 A * | 2/1998 | Wolter et al. | 556/438 |
| 5,919,885 A | 7/1999 | Wolter et al. | 528/32 |
| 6,124,491 A * | 9/2000 | Wolter et al. | 556/438 |

FOREIGN PATENT DOCUMENTS

| | | |
|---|---|---|
| DE | 4011044 | 10/1991 |
| DE | 4416857 | 6/1995 |
| DE | 19627198 | 1/1997 |
| EP | 0136680 | 4/1985 |
| EP | 0525392 | 2/1993 |

OTHER PUBLICATIONS

Chemical Abstracts 118:234 237q, Ootsuki, Toshiaki & JP 04 346993 A (Arakawa Chemical Industries, Ltd), 1993.
Chemical Abstracts 123:354510y, Ichimura, Kunihiro et al. & Mol. Cryst. Liq. Cryst. Sci. Technol., Sect. A (1995), 267, 381–6.
Chemical Abstracts 125: 116 129c Yoshinaga K. et al. & Polym. Polym. Compos. (1996) 43(3), 163–172.

* cited by examiner

*Primary Examiner*—Brian Davis
(74) *Attorney, Agent, or Firm*—Foley & Lardner LLP

(57) ABSTRACT

The invention relates to hydrolyzable and polymerizable silanes of formula (I), methods of preparing the same, and their use in the production of silica polycondensates, silica heteropolycondensates, polymers, heteropolymers, and other products.

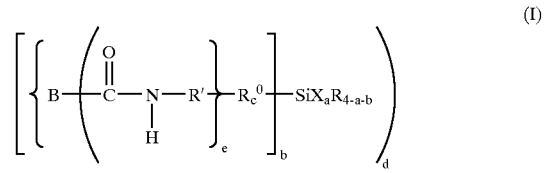

(I)

B=straight-chain or branched substituted or unsubstituted organic radical having 2 to 50 carbon atoms comprising one or more acrylate and/or methacrylate groups, the —CO—NH— group in the formula I being bonded to a carbon atom of the radical B, and B containing no norbornene, bicyclo[2.2.2]oct-2-ene or 7-oxabicyclo [2.2.1]hept-2-ene group;

R=optionally substituted alkyl, alkenyl, aryl, alkylaryl or arylalkyl, each having 1 to 15 carbon atoms, it being possible for these radicals to contain oxygen and/or sulfur and/or nitrogen atoms;

$R^o$=optionally substituted alkylene, alkenylene, arylene, alkylenearylene or arylenealkylene, each having 1 to 15 carbon atoms, it being possible for these radicals to contain oxygen and/or sulfur and/or nitrogen atoms;

R'=optionally substituted alkylene, alkenylene, arylene, alkylenearylene or aryleneakylene, each having 1to 15 carbon atoms, it being possible for these radicals to contain oxygen and/or sulfur and/or nitrogen atoms;

X=hydrogen, halogen, hydroxyl, alkoxy, acyloxy, alkylcarbonyl, alkoxycarbonyl or $NR''_2$, where R" is hydrogen, alkyl or aryl;

a=1, 2 or 3;

b=1, 2 or 3, and a+b=2, 3 or 4;

c=0 or 1;

d=1, 2, 3, 4, 5, 6, 7, 8, 9 or 10;

e=1.

19 Claims, No Drawings

HYDROLYZABLE AND POLYMERIZABLE SILANES

The invention relates to hydrolyzable and polymerizable silanes, a process for their preparation and their use for the preparation of silica polycondensates or silica heteropolycondensates and for the preparation of polymers or heteropolymers.

Hydrolyzable, organically modified silanes are widely used in the production of scratch-resistant coatings for a very wide range of substrates, and for the production of fillers, of adhesives and sealing compounds of moldings. These silanes are condensed hydrolytically either alone, as mixtures or in the presence of further hydrolyzable and/or condensable components, the final curing being effected thermally or photochemically or by redox initiation.

Thus, for example, DE 3407087 C2 discloses scratch-resistant coatings which form as a result of hydrolytic condensation of a mixture which comprises, inter alia, a hydrolyzable titanium or zirconium compound and a hydrolyzable organofunctional silane $R'_m(R''Y)_nSiX_{(4-m-n)}$, where R' is, for example, alkyl or alkenyl, R" is, for example, alkylene or alkenylene and X is a hydrolyzable radical.

DE 3536716 A1 discloses, for example, adhesives and sealing compounds which have been obtained by hydrolytic condensation of one or more organosilanes of the general formula $R_mSiX_{4-m}$ and, if desired, one or more of the components $SiX_4$ and/or $R_n(R''Y)_pSiX_{4-n-p}$, where R and R" are, for example, alkyl, alkenyl, aryl, alkylaryl, arylalkyl, alkenylaryl or arylalkenyl, X is, for example, hydrogen, halogen, hydroxyl, alkoxy or acyloxy and Y is, for example, a halogen or an optionally substituted amino, amido, aldehyde, alkylcarbonyl, carboxyl, hydroxyl, mercapto or cyano group.

Furthermore, commercial silanes having reactive double bonds, such as, for example, (meth)acryloyloxysilanes of the following type

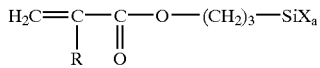

where R is hydrogen or methyl and X is, for example, halogen or alkoxy, are known. These silanes are hydrolyzable and polymerizable and can be used for the preparation of the abovementioned systems. They have the major advantage that the resulting coating, the resulting filler, adhesive or sealing compound or the resulting molding can be cured by polymerization at the reactive double bond, thermally, photochemically or by redox initiation.

Commercial silanes having reactive double bonds, such as, for example, the abovementioned (meth)acryloyloxysilanes, are in general monofunctional compounds having a C=C double bond and as a rule have a low molecular weight and, prior to the Si—X hydrolysis and condensation, are therefore relatively volatile compounds which are toxicologically unsafe owing to the acryloyl group present. In the further processing by polymerization or modified functionalization, these silanes also have the disadvantage that, owing to the presence of only one C=C double bond, only chain polymers are obtainable and, in the case of prior functionalization, this C=C double bond necessary for the organic polymerization is generally lost. Furthermore, as a rule only a short chain is present between the double bond and the silicon capable of forming an inorganic network, so that the mechanical properties (flexibility, etc.) can be varied only within narrow limits via the organic groups.

Although DE 4011044 C2 and DE 4416857 C1 disclose hydrolyzable and polymerizable silanes which have more than one reactive C=C double bond and in which the distance between the reactive double bond and the silicon capable of forming an inorganic network is longer, there is still a need for an improvement, also with respect to the functionalization of the molecule.

It is therefore an object of the present invention to provide novel, organically modified silanes which are hydrolyzable and polymerizable and which, alone, as mixtures or together with other hydrolyzable, condensable or polymerizable components, can be processed to give scratch-resistant coatings, fillers, adhesives or sealing compounds, moldings or embedding materials. These silanes should be capable of being used universally and it should be possible to incorporate them in an inorganic-organic composite system, i.e. in an inorganic-organic network. Furthermore, these silanes should be capable of being prepared rapidly and simply, i.e. without a complicated synthesis process. Furthermore, the distance between silicon and reactive double bond should be freely adjustable, and the silane should moreover have a plurality of C=C double bonds.

This object is achieved by hydrolyzable and polymerizable silanes of the general formula I

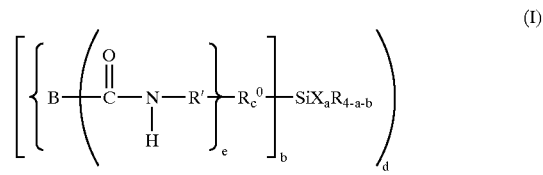

in which the radicals and indices have the following meaning:

B=straight-chain or branched organic radical having 2 to 50 carbon atoms and at least one C=C double bond, the —CO—NH— group being bonded to a carbon atom of the radical B, and B containing no norbornene, bicyclo[2.2.2]oct-2-ene or 7-oxabicyclo[2.2.1]hept-2-ene group;

R=optionally substituted alkyl, alkenyl, aryl, alkylaryl or arylalkyl, each having 1 to 15 carbon atoms, it being possible for these radicals to contain oxygen and/or sulfur and/or nitrogen atoms;

$R^o$=optionally substituted alkylene, alkenylene, arylene, alkylenearylene or arylenealkylene, each having 1 to 15 carbon atoms, it being possible for these radicals to contain oxygen and/or sulfur and/or nitrogen atoms;

R'=optionally substituted alkylene, alkenylene, arylene, alkylenearylene or aryleneakylene, each having 1 to 15 carbon atoms, it being possible for these radicals to contain oxygen and/or sulfur and/or nitrogen atoms;

X=hydrogen, halogen, hydroxyl, alkoxy, acyloxy, alkylcarbonyl, alkoxycarbonyl or $NR''_2$, where R" is hydrogen, alkyl or aryl;

a=1, 2 or 3;

b=1, 2 or 3, and a+b=2, 3 or 4;

c=0 or 1;

d=1, 2, 3, 4, 5, 6, 7, 8, 9 or 10;

e=1, 2, 3 or 4, where e=1 when c=0.

The silanes of the formula I are polymerizable via the radicals B and hydrolyzable via the radicals X. An inorganic network with Si—O—Si units can be built up via hydrolyzable groups, while an organic network can be built up by the polymerization of the double bond(s) contained in the radical B.

In preferred embodiments of the silanes according to the invention, the indices b and/or d and/or e=1. Compounds of the formula Ia result when d=1, those of the formula Ib when e=1, those of the formula Ic when b=1, those of the formula Id when b=e=1, those of the formula Id when d=e=1, those of the formula If when b=d=1 and those of the formula Ig when b=d=e=1.

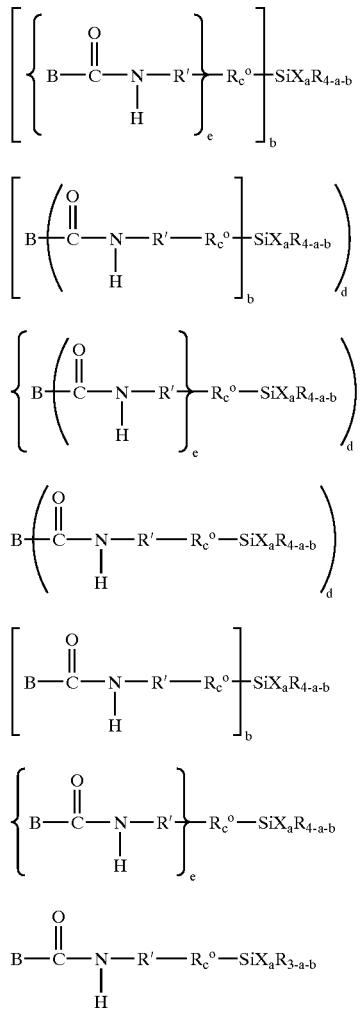

The alkyl radicals are, for example, straight-chain, branched or cyclic radicals having 1 to 15, in particular having 1 to 10, carbon atoms and preferably lower alkyl radicals having 1 to 6, particularly preferably having 1 to 4, carbon atoms. Specific examples are methyl, ethyl, n-propyl, isopropyl, n-butyl, isobutyl, sec-butyl, tert-butyl, n-pentyl, n-hexyl, cyclohexyl, 2-ethylhexyl, dodecyl and octadecyl. The hydrogen atoms of the alkyl radical may also be substituted by other atoms or groups.

The alkenyl radicals are, for example, straight-chain, branched or cyclic radicals having 2 to 15, preferably having 2 to 10, carbon atoms and preferably lower alkenyl radicals having 2 to 6 carbon atoms, such as, for example, vinyl, alkyl and 2-butenyl.

Preferred aryl radicals are phenyl, biphenyl and naphthyl. The alkoxy, acyloxy, alkylamino, dialkylamino, alkylcarbonyl, alkoxycarbonyl, arylalkyl, alkylaryl, alkylene and alkylenearylene radicals are preferably derived from the abovementioned alkyl and aryl radicals. Specific examples are methoxy, ethoxy, n-propoxy and isopropoxy, n-, iso-, sec- and tert-butoxy, monomethylamino, monoethylamino, dimethylamino, diethylamino, N-ethylanilino, acetyloxy, propionyloxy, methylcarbonyl, ethylcarbonyl, methoxycarbonyl, ethoxycarbonyl, benzyl, 2-phenylethyl and tolyl.

The alkylene, arylene, alkylenearylene and arylenealkylene radicals are preferably derived from the abovementioned alkyl and aryl radicals. Examples of preferred alkylene radicals are $-CH_2-$, $-C_2H_4-$, $-C_3H_6-$ and $-C_4H_8-$. Said radicals can optionally carry one or more substituents, for example halogen, alkyl, hydroxyalkyl, alkoxy, aryl, aryloxy, alkylcarbonyl, alkoxycarbonyl, furfuryl, tetrahydrofurfuryl, amino, monoalkylamino, dialkylamino, trialkylamino, amido, hydroxyl, formyl, carboxyl, mercapto, cyano, isocyanato, nitro, epoxy, $SO_3H$ or $PO_4H_2$. Among the halogens, fluorine, chlorine and bromine are preferred and chlorine is particularly preferred.

The radical X is preferably a fluorinated alkoxy group.

Where $a \geq 2$ or $4-a-b=2$, the radicals X and R may have the same or a different meaning in each case.

The radical B is derived from a substituted or unsubstituted compound $B(COOH)d$ having at least one $C=C$ double bond, for example having vinyl, allyl, acryloyl and/or methacryloyl groups, and having 2 to 50, preferably having 2 to 30, carbon atoms. B is preferably derived from a substituted or unsubstituted compound having two or more acrylate or methacrylate groups. Such compounds are referred to below as (meth)acrylates. If the compound $B(COOH)_d$ is substituted, the substituents can be selected from the abovementioned substituents. The index d may assume values from 1 to 10, values from 1 to 4 being preferred.

In further preferred embodiments, the radical B is derived from acrylates and/or from methacrylates of trimethylolpropane, of glycerol, of pentaerythritol, of dipentaerythritol, of $C_2-C_4$-alkanediols, of polyethylene glycols, of polypropylene glycols and of optionally substituted and/or alkoxylated bisphenol A.

Without restricting the generality, further specific examples of radicals B are disclosed in DE 4416857 C1, pages 4 to 18. This disclosure is hereby especially incorporated by reference. Via its free valences, the radical B is linked in each case to an amido group $-C(O)-N(H)-$, these amido groups being bonded in each case to a carbon atom of the radical B.

The silanes according to the invention can be prepared, for example, by reacting d moles of a compound $[\{OCN-R'\}_e R^o_c]_b SiX_a R_{4-a-b}$ under decarboxylating conditions with b·e moles of a compound $B(COOH)_d$, the radicals and indices being defined as in claim 1. The general equation is as follows.

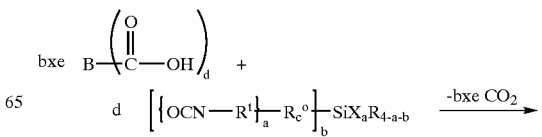

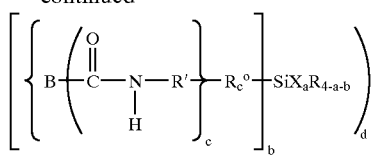

The reaction is preferably effected at from room temperature to 60° C. However, lower or higher temperatures are also possible. If the starting materials are liquid at the reaction temperature, the reaction can also be carried out without a solvent. If solvents are used, for example, THF, toluene and ethyl acetate are suitable. Particularly good results are obtained if the solvents used are dried. In order to accelerate the reaction, catalysts may also be used. Suitable catalysts are, for example, tertiary amines, such as, for example, DABCO (1,4-diazocyclo[2.2.2]-octane). If the compound [{OCN—R'}$_e$R$^o_c$]$_b$SiX$_a$R$_{4-a-b}$ is used in excess, the resulting silane according to the invention has free carboxyl groups on the radical B.

Without restricting the generality, specific examples of radicals —R'—R$^o$SiX$_a$R$_{3-a}$ are mentioned below, where n assumes the values 1 to 10 in each case. —(CH$_2$)$_n$—Si(CH$_3$)$_2$(OC$_2$H$_5$), —(CH$_2$)$_n$—Si(CH$_3$)(OC$_2$H$_5$)$_2$, —(CH$_2$)$_n$—Si(OC$_2$H$_5$)$_3$, —(CH$_2$)$_n$—Si(C$_2$H$_5$)$_2$(OCH$_3$), —(CH$_2$)$_n$—Si(C$_2$H$_5$)(OCH$_3$)$_2$, —(CH$_2$)$_n$—Si(OCH$_3$)$_3$, —(CH$_2$)$_n$—Si(CH$_3$)$_2$(OCH$_3$), —(CH$_2$)$_n$—Si(CH$_3$)(OCH$_3$)$_2$, —(CH$_2$)$_n$—Si(C$_2$H$_5$)$_2$(OC$_2$H$_5$), —(CH$_2$)$_n$—Si(C$_2$H$_5$)(OC$_2$H$_5$)$_2$, —(CH$_2$)$_n$—Si(CH$_3$)(C$_2$H$_5$)(OCH$_3$), —(CH$_2$)$_n$—Si(CH$_3$)(C$_2$H$_5$)(OC$_2$H$_5$), —(CH$_2$)$_n$—Si(CH$_3$)(OC$_2$H$_5$)(OCH$_3$), —(CH$_2$)$_n$—Si(C$_2$H$_5$)(OC$_2$H$_5$)(OCH$_3$), —(CH$_2$)$_n$—Si(OC$_2$H$_5$)$_2$(OCH$_3$), —(CH$_2$)$_n$—Si(OC$_2$H$_5$)(OCH$_3$)$_2$, —(CH$_2$)$_n$—Si(CH$_3$)(OC(CH$_3$)=CH$_2$)$_2$, —(CH$_2$)$_n$—Si(C$_2$H$_5$)(OC(CH$_3$)=CH$_2$)$_2$, —(CH$_2$)$_n$—Si(CH$_3$)$_2$(OC(CH$_3$)=CH$_2$), —(CH$_2$)$_n$—Si(C$_2$H$_5$)$_2$(OC(CH$_3$)=CH$_2$), —(CH$_2$)$_n$—Si(OCH$_3$)(OC(CH$_3$)=CH$_2$)$_2$, —(CH$_2$)$_n$—Si(OC$_2$H$_5$)(OC(CH$_3$)=CH$_2$)$_2$, —(CH$_2$)$_n$—Si(OCH$_3$)$_2$(OC(CH$_3$)=CH$_2$), —(CH$_2$)$_n$—Si(OC$_2$H$_5$)$_2$(OC(CH$_3$)=CH$_2$), —(CH$_2$)$_n$—Si(C$_6$H$_5$)(OC$_2$H$_5$)$_2$, —(CH$_2$)$_n$—Si(C$_6$H$_5$)(OCH$_3$)$_2$, —(CH$_2$)$_n$—Si(C$_6$H$_5$)(OCH$_3$)(OC$_2$H$_5$), —(CH$_2$)$_n$—Si(C$_6$H$_5$)(OC(CH$_3$)=CH$_2$)$_2$.

The silanes according to the invention are stable compounds and can be processed, either alone or together with other hydrolyzable, condensable and/or polymerizable components, to give silica polycondensates or to give silica heteropolycondensates, whose final curing is then effected by polymerization of the C=C double bonds. However, the silanes according to the invention can also be processed alone or together with other hydrolyzable, condensable and/or polymerizable components to give polymers which can then be solidified by subsequent hydrolytic condensation.

Silica(hetero)polycondensates which are modified with organic groups and processes for their preparation (for example starting from hydrolytically condensable organosilanes by the sol-gel process) are known in large number. As already mentioned at the outset, such condensates are used for a very wide range of purposes, for example as molding materials, as paints for coatings, etc. Owing to the wide range of potential uses of this class of substances, however, there is also a continuous need for modification of the already known condensates, on the one hand in order thus to open up new applications and, on the other hand, further to optimize their properties for specific intended uses.

The silanes according to the invention are hydrolyzable and condensable in a basic or acidic medium without linkage of the C=C double bond taking place as a result. It is thus possible to incorporate the silanes according to the invention into an inorganic-organic network by hydrolytic condensation. The silanes according to the invention contain hydrolyzable groups X, for example alkoxy groups, so that an inorganic network having Si—O—Si units can thus be built up, while the C=C double bonds contained in the radical B can be polymerized with synthesis of an organic network. It is thus possible to replace organically modified, hydrolyzable and condensable silanes, for example in coatings, fillers, adhesives and sealing compounds, in moldings and in embedding materials according to the prior art, by the silanes according to the invention.

In order to synthesize the inorganic network, the silanes according to the invention, optionally with addition of other cocondensable components, are subjected to hydrolysis and polycondensation. The polycondensation is preferably effected by the sol-gel process, as described, for example, in DE-A1 2758414, 2758415, 3011761, 3826715 and 3835968.

In order to synthesize the organic network, the silanes according to the invention, optionally with addition of other copolymerizable components, are polymerized. The polymerization can be effected, for example, thermally or photochemically or by redox initiation with the use of methods as described, for example, in DE-A1 3143820, 3826715 and 3835968. A combination of these methods is also possible.

Compounds which are capable of undergoing free radical and/or ionic and/or covalent nucleophilic polymerization can be added as further copolymerizable components. Compounds which are capable of free radical polymerization and may be added are, for example, those having C=C double bonds, such as, for example, acrylates or methacrylates, the polymerization being effected via the C=C double bonds. Ionically polymerizable compounds which may be added contain, for example, ring systems capable of undergoing ring-opening cationic polymerization, such as, for example, spiroorthoesters, spiroorthocarbonates, bicyclic spiroorthoesters, mono- or oligoepoxides or spirosilanes, as disclosed in DE 4125201 C1. However, compounds capable of both ionic and free radical polymerization, such as, for example, methacryloylspiroorthoesters, may also be added. These are polymerizable by a free radical method via the C=C double bond and cationically with ring opening. The preparation of these systems is described, for example, in Journal f. prakt. Chemie, Volume 330, Part 2, 1988, pages 316–318. Furthermore, the silanes according to the invention can be used in systems as described, for example, in DE 4405261.

It is also possible to add other known, silane-bonded cyclic systems which can be incorporated as polymerized units. Said systems are, for example, those which contain epoxides. Such systems are described in the preparation of the spirosilanes, in DE 4125201 C1.

The silanes according to the invention are highly reactive systems which lead to poly(hetero)condensates which, on UV irradiation, lead to mechanically stable coatings or moldings or fillers within a very short time. The silanes according to the invention can be prepared by simple addition reactions and have a variable number of reactive groups of different functionalities through a suitable choice of the starting compounds.

When two or more C=C double bonds are present in the radical B, the formation of a three-dimensional, organic network is possible. The mechanical properties (e.g. flexibility) and the physicochemical properties (e.g. adsorption, refractive index, adhesion, etc.) of the poly (hetero)condensates can be influenced by the distance between the Si atom and the radical B, i.e. by the chain length, by the presence of further functional groups in this chain and by the structure of this chain (linear or branched). By the formation of an inorganic network, silicone-like or glassy properties of the poly(hetero)condensates can be established, depending on the type and number of the hydrolyzable groups (e.g. alkoxy groups).

The silanes according to the invention have relatively high molecular weights and accordingly lower volatility than pure (meth)acrylate monomers, so that the toxic hazard during processing and application is lower. In the case of the inorganic and/or organic network formation, polysiloxanes having further reduced volatility form and thus completely eliminate the toxicity problem of the acrylate components.

If the possibilities for varying the cocondensable and copolymerizable components are then also taken into account, it becomes evident that silica (hetero) polycondensates are provided via the silanes according to the invention, which (hetero)polycondensates can be adapted in a varied manner to prescribed fields of use and can therefore be used in all areas where silica(hetero) polycondensates are already used, but also open up new potential applications, for example in the area of optics, of electronics, of medicine, of optoelectronics and of packaging materials for foods, etc. Particularly in the dental sector, the silica(hetero)polycondensates prepared using the silanes according to the invention have major advantages owing to low shrinkage, the inorganic structure, the favorable abrasion behavior and the high molecular weights of the monomers or the possible omission of additional reactive monomers.

The silanes according to the invention can be used either as such or in compositions which additionally contain additives adapted to the intended use, for example conventional coating additives, solvents, fillers, photoinitiators, thermal initiators, levelling agents and pigments. The silanes according to the invention or the silane-containing compositions are suitable, for example, for the production of coating materials, fillers or bulk materials, of adhesives and injection molding materials, of fibers, particles, films, adhesion promoters, of impression compounds, of dental restoration materials and of embedding materials. Coatings and moldings comprising the silanes according to the invention have the advantage that they are photochemically structurable. Specific applications are, for example, the coating of substrates of metal, plastic, paper, ceramic, etc. by immersion, pouring, brushing, spraying, electrostatic spraying, electrodip coating, etc., use for optical, optoelectrical or electronic components, the production of fillers, the production of scratch-resistant, abrasion-resistant, corrosion-resistant coatings, the production of moldings, for example by injection molding, die casting, compression molding, rapid prototyping or extrusion, and the production of composites, for example of fibers, fillers or woven fabrics.

In addition to the silanes of the formula (I), according to the invention, further hydrolytically condensable compounds of silicon, of boron, of aluminum, of phosphorus, of tin, of lead, of the transition metals or of the lanthanides or actinides can also be used. These compounds can be employed either as such or ready in precondensed form for the preparation of the polycondensates. It is preferable if at least 10 mol %, in particular at least 80 mol % and especially at least 90 mol %, based on monomeric compounds, of the starting materials used for the preparation of the silica (hetero)polycondensates are silicon compounds.

It is also preferable if the silica(hetero)polycondensates are based on at least 1 mol %, for example from 25 to 100 mol %, in particular from 50 to 100 mol %, especially from 75 to 100 mol %, based on monomeric compounds, of one or more of the silanes according to the invention.

Particularly preferred among the hydrolytically condensable silicon compounds which differ from silanes of the general formula (I) and can be optionally used are those of the general formula (II)

$$R_a(R''Z')_b SiX_{4-(a+b)} \qquad (II)$$

in which the radicals R, R", X and Z' are identical or different and have the following meaning:

R=Alkyl, alkenyl, aryl, alkylaryl or arylakyl,

R"=Alkylene or alkenylene, these radicals may be interrupted by oxygen or sulfur atoms or —NH— groups, X=Hydrogen, halogen, hydroxyl, alkoxy, acyloxy, alkylcarbonyl, alkoxycarbonyl or NR'$_2$, where R'=hydrogen, alkyl or aryl, Z'=Halogen or an optionally substituted amino, amido, aldehyde, alkylcarbonyl, carboxyl, mercapto, cyano, alkoxy, alkoxycarbonyl, sulfo, phosphoric acid, acryloyloxy, methacryloyloxy, epoxy or vinyl group, a=0, 1, 2 or 3 and b=0, 1, 2 or 3, where a+b=1, 2 or 3.

Such silanes are described, for example, in DE 34 07 087 C2.

Also preferred among the hydrolytically condensable silicon compounds which differ from silanes of the general formula (I) and can optionally also be used are those of the general formula (III)

$$\{X_n R_k Si[(R^2 A)_l]_{4-(n+k)}\}_x B \qquad (III)$$

in which the radicals A, R, R$^2$ and X are identical or different and have the following meaning:

A=O, S, PR', POR', NHC(O)O or NHC(O)NR', where R'=hydrogen, alkyl or aryl,

B=straight-chain or branched organic radical which is derived from a compound B' having at least one (for l=1 and A=NHC(O)O or NHC(O)NR') or at least two C═C double bonds and from 5 to 50 carbon atoms, where R'=hydrogen, alkyl or aryl, R=alkyl, alkenyl, aryl, alkylaryl or arylalkyl, R$^2$=alkylene, arylene or alkylenearylene, X=hydrogen, halogen, hydroxyl, alkoxy, acyloxy, alkylcarbonyl, alkoxycarbonyl or NR'$_2$, where R'=hydrogen, alkyl or aryl, n=1, 2 or 3, k=0, 1 or 2, l=0 or 1 and x=a number whose maximum value corresponds to the number of double bonds in the compound B' minus 1 or is equal to the number of double bonds in the compound B' when l=1 and A is NHC(O)O or NHC (O)NR'.

Such silanes are described in DE 40 11 044 and in EP 91 105 355.

Also particularly preferred among the hydrolytically condensable silicon compounds which differ from silanes of the general formula (I) and can optionally also be used are those of the general formula (IV)

$$Y_n SiX_m R_{4-(n+m)} \qquad (IV)$$

in which the radicals X, Y and R are identical or different and have the following meaning:

R=alkyl, phenyl, aryl, alkylaryl or arylalkyl,

X=hydrogen, halogen or hydroxyl, alkoxy, acyloxy, alkylcarbonyl, alkoxycarbonyl or $NR'_2$, where R'=hydrogen, alkyl or aryl, Y=a substituent which contains a substituted or unsubstituted 1,4,6-trioxospiro[4,4]nonane radical, n=1, 2 or 3 and m=1, 2 or 3, where n+m≦4.

These spirosilanes are hydrolyzable via the radicals X and polymerizable via the radicals Y, and they are described in great detail in DE 4125201 C1.

Also particularly preferred among the hydrolytically condensable silicon compounds which differ from silanes of the general formula (I) and can also optionally be used are those of the general formula (V)

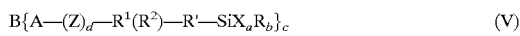

$$B\{A\text{---}(Z)_d\text{---}R^1(R^2)\text{---}R'\text{---}SiX_aR_b\}_c \qquad (V)$$

in which the radicals and indices have the following meaning:

B=a straight-chain or branched organic radical having at least one C=C double bond and from 4 to 50 carbon atoms;

X=hydrogen, halogen, hydroxyl, alkoxy, acyloxy, alkylcarbonyl, alkoxycarbonyl or $NR''_2$;

R=alkyl, alkenyl, aryl, alkylaryl or arylalkyl;

R'=alkylene, arylene, arylenealkylene or alkylenearylene, each having from 0 to 10 carbon atoms, it being possible for these radicals to be interrupted by oxygen and sulfur atoms or by amino groups;

R''=hydrogen, alkyl or aryl;

A=O, S or NH for
  d=1 and
  Z=CO and
  $R^1$=alkylene, arylene or alkylenearylene, each having from 1 to 10 carbon atoms, it being possible for these radicals to be interrupted by oxygen and sulfur atoms or amino groups,
  $R^2$=COOH or H; or A=O, S, NH or COO for
  d=1 and
  Z=CHR, where R is H, alkyl, aryl or alkylaryl and
  $R^1$=alkylene, arylene or alkylenearylene, each having 1 to 10 carbon atoms, it being possible for these radicals to be interrupted by oxygen and sulfur atoms or by amino groups, and
  $R^2$=OH; or A=O, S, NH or COO for
  d=0 and
  $R^1$ =alkylene, arylene or alkylenearylene, each having from 1 to 10 carbon atoms, it being possible for these radicals to be interrupted by oxygen and sulfur atoms or by amino groups, and
  $R^2$=OH; or A=S for
  d=1 and
  Z=CO and
  $R^1$=N and
  $R^2$=H;

a=1, 2 or 3;

b=0, 1 or 2, where a+b=3;

c=1, 2, 3 or 4.

Said silanes are described in DE 44 16 857 C1.

Among the optionally used hydrolyzable aluminum compounds, those which have the general formula $AlR°_3$, in which the radical R°, which may be identical or different, are selected from halogen, alkoxy, alkoxycarbonyl and hydroxyl, are particularly preferred. Regarding the more exact (preferred) definitions of these radicals, reference may be made to the statements in connection with the silanes according to the invention. Some or all of the abovementioned groups may also be replaced by chelate ligands (e.g. acetylacetone or acetoacetate, acetic acid).

Particularly preferred aluminum compounds are aluminum alkoxides and halides. In this context, the following may be mentioned as specific examples $Al(OCH_3)_3$, $Al(OC_2H_5)_3$, $Al(O\text{-}n\text{-}C_3H_7)_3$, $Al(O\text{-}i\text{-}C_3H_7)_3$, $Al(OC_4H_9)_3$, $Al(O\text{-}i\text{-}C_4H_9)_3$, $Al(O\text{-}s\text{-}C_4H_9)_3$, $AlCl_3$, $AlCl(OH)_2$.

Compounds liquid at room temperature, such as, for example, aluminum sec-butylate and aluminium isopropylate, are particularly preferred.

Suitable hydrolyzable titanium and zirconium compounds which can optionally be used are those of the general formula $MX_yR_z$, in which M is Ti or Zr, y is an integer from 1 to 4, in particular from 2 to 4, z is 0, 1, 2 or 3, preferably 0, 1 or 2, and R are as defined in the case of the general formula (I). This also applies to the preferred meanings. Particularly preferably, the compounds of the formula $MX_yR_z$ are those in which y is 4.

As in the case of the above aluminium compounds, complexed titanium or zirconium compounds may also be used. Additional preferred complexing agents here are acrylic acid and methacrylic acid, and silanes according to the invention which have acrylate or methacrylate groups may also be used for complexing. In this case, the major advantage of the silanes according to the invention is that no additional complexing agents have to be used for complexing titanium and/or zirconium compounds.

Specific examples of zirconium and titanium compounds which may be used are the following: $TiCl_4$, $Ti(OC_2H_5)_4$, $Ti(OC_3H_7)_4$, $Ti(O\text{-}i\text{-}C_3H_7)_4$, $Ti(OC_4H_9)_4$, $Ti(2\text{-ethylhexyloxy})_4$, $ZrCl_4$, $Zr(OC_2H_5)_4$, $Zr(OC_3H_7)_4$, $Zr(O\text{-}i\text{-}C_3H_7)_4$, $Zr(O\text{-}i\text{-}C_3H_7)_4$, $Zr(OC_4H_9)_4$, $Zr(2\text{-ethylhexyloxy})_4$, $ZrOCl_2$.

Further hydrolyzable compounds which may be used for the preparation of the polyheterocondensates are, for example, boron trihalides and boric acid esters, such as, for example, $BCl_3$, $B(OCH_3)_3$ and $B(OC_2H_5)_3$, tin tetrahalides and tin tetraalkoxides, such as, for example, $SnCl_4$ and $Sn(OCH_3)_4$, and vanadyl compounds, such as, for example, $VOCl_3$ and $VO(OCH_3)_3$.

The silanes according to the invention need not necessarily be isolated for further processing to give poly(hetero) condensates. It is also possible and preferred, in a one-pot process, first to prepare these silanes and then—optionally after addition of further hydrolyzable compounds—to condense them hydrolytically. This reaction procedure represents a major advantage of the silanes according to the invention and the processing thereof to give polycondensates.

As already mentioned, the preparation of the poly(hetero) condensates can be effected in a manner customary in this area. If virtually exclusively silicon compounds are used, the hydrolytic condensation can in most cases be carried out by adding (preferably with stirring and in the presence of a hydrolysis and condensation catalyst) the required water, at room temperature or with slight cooling, directly to the silicon compounds to be hydrolyzed, which are present either as such or in solution in a suitable solvent, and then stirring the resulting mixture for some time (from one to several hours).

In the presence of reactive compounds aluminum, titanium or zirconium, it is as a rule advisable to add the water gradually. Regardless of the reactivity of the compounds present, the hydrolysis is effected as a rule at temperatures of from −20 to 130° C., preferably from 0 to 30° C. or at the boiling point of the optionally used solvent. As already indicated, the best method of water addition depends in particular on the reactivity of the starting compounds used. Thus, for example, the dissolved starting compounds can slowly be added dropwise to an excess of water, or water is added in one portion or in portions to the optionally dissolved starting compounds. It may also be useful not to add the water as such but to introduce it into the reaction system with the aid of water-containing organic or inorganic systems. In many cases, the introduction of the amount of water into the reaction mixture with the aid of moisture-laden adsorbance, for example of molecular sieves, and of water-containing, organic solvents, for example of 80% ethanol, has proven particularly suitable. However, the addition of water can also be effected by means of a chemical reaction in which water is liberated in the course of the reaction. Examples of this are esterifications.

If a solvent is used, ketones, preferably lower dialkyl ketones, such as acetone or methyl isobutyl ketone, ethers, preferably lower dialkyl ethers, such as diethyl ether or dibutyl ether, THF, amides, esters, in particular ethyl acetate, dimethylformamide, amines, in particular triethylamine, and mixtures thereof are also suitable in addition to the lower aliphatic alcohols (e.g. ethanol or isopropanol).

If spirosilanes are used for the preparation of the poly (hetero)condensates, hydrolysis is preferably carried out in a medium which is basic with respect to the spirosilanes. This is produced either by a basic solvent, such as, for example, by triethylamine, or by addition of basic hydrolysis and condensation catalysts, such as, for example, $NH_3$, NaOH, KOH, methylimidazole, etc.

The starting compounds need not necessarily all be present at the beginning of the hydrolysis (polycondensation), but it may even prove advantageous in certain cases if only some of these compounds are initially brought into contact with water and the remaining compounds are added later.

In order to avoid as far as possible precipitates during the hydrolysis and the polycondensation, in particular with the use of hydrolyzable compounds differing from silicon compounds, the addition of water can be effected in a plurality of stages, for example in three stages. In the first stage, for example, a tenth to a twentieth of the amount of water required for the hydrolysis can be added. After brief stirring, the addition of a fifth to a tenth of the required amount of water can be effected and, after further brief stirring, the remainder can finally be added.

The condensation time depends on the respective starting components and their amounts, the optionally used catalyst, the reaction temperature, etc. In general, the polycondensation is effected at atmospheric pressure but may also be carried out at superatmospheric or reduced pressure.

The poly(hetero)condensate thus obtained can be further processed either as such or after partial or virtually complete removal of the solvent used. In some cases, it may prove advantageous if, in the product obtained after the polycondensation, the excess water and the resulting and optionally additionally used solvent are replaced by another solvent in order to stabilize the poly(hetero)condensate. For this purpose, the reaction mixture can be thickened, for example in vacuo at slightly elevated temperature, to such an extent that it can still be taken up by another solvent without problems.

If these poly(hetero)condensates are to be used as coating materials, for example for coating plastics (such as, for example, PVC, PC, PMMA, PE, PS, etc., of glass, paper, wood, ceramic, metal, etc.), customary coating additives, such as, for example, colorants (pigments or dyes), fillers, antioxidants, flameproofing agents, leveling agents, UV absorbers, stabilizers or the like, may also optionally be added to them at the latest prior to use. Additives for increasing the conductivity (for example, graphite powder, silver powder, etc.) also deserve to be mentioned in this context. In the case of the use as molding material, the addition of inorganic and/or organic fillers, such as, for example, organic and inorganic particles, (glass) fibers, minerals, etc., is particularly suitable.

The final curing of the poly(hetero)condensates is effected thermally, by redox initiation or photochemically after the addition of suitable initiators, it also being possible for a plurality of curing mechanisms to take place simultaneously and/or in succession. In the course of the polymerization, the C=C double bonds are produced and the organic network is built up. Owing to the relatively high molecular weights of the silanes according to the invention, they undergo only slight volume shrinkage during curing.

It is also possible to add further components capable of ionic and/or free radical and/or covalent nucleophilic polymerization to the poly(hetero)condensates before the final curing, i.e. before the polymerization. Compounds which are capable of free radical copolymerization and which may be added are, for example, those having C=C double bonds, such as, for example, acrylates or methacrylates, the polymerization taking place via the C=C double bonds. Compounds which are capable of ionic copolymerization and which may be added contain, for example, ring systems capable of ring-opening cationic polymerization, such as, for example, spiroorthoesters, spiroorthocarbonates, bicyclic spiroorthoesters, mono- or oligoepoxides or spirosilanes of the general formula IV. However, it is also possible to add compounds capable of both cationic and free radical polymerization, such as, for example, methacryloylspiroorthoesters. These can undergo free radical polymerization by the C=C double bond and cationic polymerization with ring opening. These systems are described, for example, in Journal f. prakt. Chemie, Volume 330, Part 2, 1988, pages 316–318, or in Journal of Polymer Science: Part C: Polymer Letters, Vol. 26, pages 517–520 (1988).

If the curing of the poly(hetero)condensates is effected photochemically, photoinitiators are added to it, thermal initiators are added in the case of thermal curing and initiator-activator systems are added in the case of redox-initiated curing.

The initiator can be added in customary amounts. Thus, initiators can be added in an amount of, for example, from 0.5 to 5% by weight, in particular from 1 to 3% by weight, based on the mixture, for example to a mixture which contains from 30 to 50% by weight of solid (polycondensate).

If, in addition to the silanes according to the invention, further components which contain reactive double bonds, such as, for example, silanes according to the general formula (III), are used for the preparation of the poly(hetero) condensates, a polymerization which can be initiated thermally and/or photochemically and/or by redox initiators can likewise take place via these double bonds.

Photoinitiators used may be, for example, the commercially available ones. Examples of these are Irgacure 184 (1-hydroxycyclohexyl phenyl ketone), Irgacure 500 (1-hydroxycyclohexyl phenyl ketone/benzophenone) and other photoinitiators of the Irgacure type available from Ciba-Geigy: Darocure 1173, 1116, 1398, 1174 and 1020

(available from Merck), benzophenone, 2-chlorothioxanthone, 2-methylthioxanthone, 2-isopropylthioxanthone, benzoin, 4,4'-dimethoxybenzoin, etc. If the curing is effected using visible light, such as, for example, in the dental sector, the initiator used may be, for example, camphorquinone.

Particularly suitable thermal initiators are organic peroxides in the form of diacyl peroxides, peroxodicarbonates, alkyl peresters, dialkyl peroxides, perketals, ketone peroxides and alkyl hydroperoxides. Specific and preferred examples of thermal initiators are dibenzoyl peroxide, 1-butyl perbenzoate and azobisisobutyronitrile.

The initiator/activator systems used may be those which are customary for this purpose, such as, for example, aromatic amines (e.g. N,N-bis(2-hydroxyethyl)-p-toluidine), and the activators or initiators used may be, for example, dibenzoyl peroxide, it being possible to set the curing time according to the respective application via the concentration thereof or the concentration ratio thereof. Further amines are mentioned, for example, in DE 4310733.

In the case of covalent nucleophilic curing, for example, compounds having at least one amino group are added as initiators. Suitable amines are mentioned, for example, in DE 4405261.

A coating material (poly(hetero)condensate) provided with an initiator and based on the silanes according to the invention can then be used for coating substrates. Customary coating methods, for example dipping, flooding, pouring, spin-coating, roll-coating, spraying, brushing on, electrostatic spraying and electrodip coating, can be used for this coating. It should also be mentioned here that the coating material need not necessarily be solvent-containing. Particularly with the use of starting substances (silanes) having two alkoxy groups on the silicon atom, it is also possible to work without adding solvents.

Before the curing, the applied coat is preferably allowed to dry. Then, depending on the type of initiator, it can be cured by redox initiation, thermally or photochemically in a manner known per se. Combinations of curing methods are of course also possible.

If the curing of the applied coat is effected by irradiation, it may prove advantageous to carry out thermal curing after the radiation curing, in particular to remove any solvent still present or to include further reactive groups in the curing. Although polymerizable groups are already present in the poly(hetero)condensates based on the silanes according to the invention, it may prove advantageous in certain cases to add further compounds (preferably of purely organic nature) having, for example, unsaturated groups to these condensates before or during their further processing. Preferred examples of such compounds are acrylic acid and methacrylic acid and compounds derived therefrom, in particular esters of preferably monohydric alcohols (e.g. $C_{1-4}$-alkanols), (meth)acrylonitrile, styrene and mixtures thereof. When the poly(hetero)condensates are used for the preparation of coating materials, such compounds can simultaneously act as solvents or diluents.

The production of moldings or molding materials from poly(hetero)condensates based on the silanes according to the invention can be effected by any method customary in this field, for example by compression molding, injection molding, die casting, extrusion, etc. The poly(hetero)condensates based on the silanes according to the invention are also suitable for the production of composite materials (for example with glass fiber reinforcement).

A further potential application of the silanes according to the invention is for the preparation of hydrolytically condensable polymers. For this purpose, the silanes according to the invention are polymerized, alone or together with other components capable of free radical and/or ionic and/or covalent nucleophilic copolymerization, the final curing then being effected by hydrolytic condensation via the hydrolyzable groups of the silanes according to the invention and possibly of further, hydrolyzable components. In this case, the organic network is first built up by polymerization and the inorganic one is then built up by hydrolytic condensation.

The polymers are prepared by free radical and/or ionic and/or covalent nucleophilic polymerization of one or more C=C double bond-containing compounds and optionally other compounds capable of free radical and/or ionic and/or covalent nucleophilic polymerization, by redox initiation and/or by the action of heat and/or of electromagnetic radiation, optionally in the presence of one or more initiators and/or of a solvent, and, in said preparation, from 1 to 100 mol percent, based on monomeric compounds, of the C=C double bond-containing compounds is selected from the silanes of the general formula (I) according to the invention.

However, it is also possible to add further components capable of ionic and/or free radical and/or covalent nucleophilic copolymerization to the silanes according to the invention before the polymerization. Compounds capable of free radical polymerization and which may be added are, for example, those having C=C double bonds, such as, for example, acrylates or methacrylates, the polymerization taking place via the C=C double bonds. Compounds which are capable of ionic polymerization and which may be added contain, for example, ring systems which are cationically polymerizable with ring opening, such as, for example, spiroorthoesters, spiroorthocarbonates, bicyclic bispiroorthoesters, mono- or oligoepoxides or spirosilanes of the general formula IV. However, compounds capable of both cationic and free radical polymerization, such as, for example, methacryloylspiroorthoesters, may also be added. These are capable of free radical polymerization via the C=C double bond and cationic polymerization with ring opening. These systems are described, for example, in Journal f. prakt. Chemie, Volume 330, Part 2, 1988, pages 316–318, or in Journal of Polymer Science: Part C: Polymer Letters, Vol. 26, pages 517–520 (1988).

Further hydrolyzable and polymerizable compounds of silicon may be added, optionally in precondensed form, to the silanes according to the invention before polymerization and are then incorporated as polymerized units. Such silicon compounds are derived, for example, from epoxide-containing silanes, are therefore capable of cationic polymerization and are used, inter alia, for the preparation of the spirosilanes according to DE 4125201 C1. These systems are described in DE 4125201 C1.

However, it is also possible to use silicon compounds which are derived, for example, from those of the general formula (III) and are capable of free radical polymerization. These systems have already been described in more detail in the case of the preparation of the poly(hetero)condensates.

The polymerization is effected by redox initiation and/or thermally and/or photochemically after the addition of suitable initiators. For example, C=C double bonds are produced in the course of a free radical polymerization and rings of Spiro groups and possibly further rings capable of free radical polymerization may be opened in the course of the cationic polymerization. The organic network is built up as a result. Surprisingly, it was found that the volume of the reaction material does not change or changes only slightly in the course of this polymerization. The relatively high molecular weight of the silanes according to the invention is responsible for this.

Photoinitiators are added to the reaction material if the polymerization is effected photochemically, thermal initiators are added if the polymerization is effected thermally, and initiator/activator systems are added in the case of redox-initiated polymerization.

If components having Spiro groups were added to the silanes according to the invention, polymerization which can be initiated thermally or photochemically can likewise take place via said groups. Photoinitiators which may be used for this purpose are, for example, the commercially available ones.

Initiator can be added in customary amounts. Thus, initiator in an amount of, for example, from 0.5 to 5% by weight, in particular from 1 to 3% by weight, based on the mixture, may be added, for example, to a mixture which contains from 30 to 50% by weight of solid.

In order to build up the inorganic network, the polymer obtained in this manner can then be hydrolytically condensed, optionally in the presence of further, hydrolytically condensable compounds of silicon and optionally other elements from the group consisting of B, Al, P, Sn, Pb, the transition metals, the lanthanides and the actinides, and/or precondensates derived from the abovementioned compounds, by the action of water or moisture, optionally in the presence of a catalyst and/or of a solvent. The polymers contain hydrolyzable groups X, for example alkoxy groups, so that an inorganic network (Si—O—Si units) can be built up therewith.

Preferred among the optionally used hydrolyzable compounds of silicon are those of the general formula (II), optionally in precondensed form. These systems have already been described in detail in the case of the preparation of the poly(hetero)condensates.

Particularly preferred among the optionally used hydrolyzable aluminum compounds are those which have the general formula $AlR^o{}_3$, and suitable hydrolyzable titanium and zirconium compounds which may optionally be used are those of the general formula $MX_yR_z$. These systems, too, have already been discussed in detail in the case of the preparation of the poly(hetero)condensates.

Further hydrolyzable compounds which can be added to the polymer are, for example, boron trihalides and boric acid esters, such as, for example, $BCl_3$, $B(OCH_3)_3$ and $B(OC_2H_5)_3$, tin tetrahalides and tin tetraalkoxides, such as, for example, $SnCl_4$ and $Sn(OCH_3)_4$, and vanadyl compounds, such as, for example, $VOCl_3$ and $VO(OCH_3)_3$.

As already mentioned, here too the hydrolytic condensation can be effected in a manner customary in this area. The hydrolytic condensation can be effected in most cases by adding the required water, at room temperature or with slight cooling, directly to that polymer to be hydrolyzed, which is present either as such or in solution in a suitable solvent, preferably while stirring and in the presence of a hydrolysis and condensation catalyst.

In the presence of reactive compounds of Al, Ti or Zr, gradual addition of the water is as a rule advisable here too. Regardless of the reactivity of the compounds present, here too the hydrolysis is effected as a rule at temperatures of from –20 to 130° C., preferably from 0 to 30° C., or the boiling point of the optionally used solvent. As already indicated, the best method of addition of water depends in particular on the reactivity of the starting compounds used. Thus, for example, the dissolved polymer can be slowly added dropwise to an excess of water, or water is added in a portion or in portions to the optionally dissolved polymer.

It may also be useful not to add the water as such but to introduce it into the reaction system with the aid of water-containing organic or inorganic systems.

The polyfunctional silanes according to the invention provide starting compounds which permit the preparation of inorganic-organic composite polymers having a very wide range of properties adjustable within wide ranges or the modification of existing composite polymers. The use of such a material includes various purposes and, inter alia, use as bulk material, composites, adhesives, casting and sealing compounds, coating materials, adhesion promoters and binders for ceramic particles (ceramic shaping processes), for the production or priming of fillers and fibers and of grinding disks, use in reaction extruders and in dental restoration materials. The photochemically, the thermally and the chemically (2-components, anaerobic, redox, etc.) induced reaction are suitable for the organic polymerization. The combination of self-curing with, for example, photo-initiated or thermal curing is also possible.

A particular advantage of the silanes according to the invention, for example over silanes of DE 4011044 C2 is their excellent chemical and thermal stability. The amido group of the silanes according to the invention is chemically and thermally more stable than the urethane group of the silanes of DE 4011044 C2.

The invention is explained in more detail with reference to an embodiment.

1. Synthesis of the Carboxylic Acid-modified Dimethacrylate

First, a carboxylic acid-modified dimethacrylate is prepared by customary methods according to the following equation.

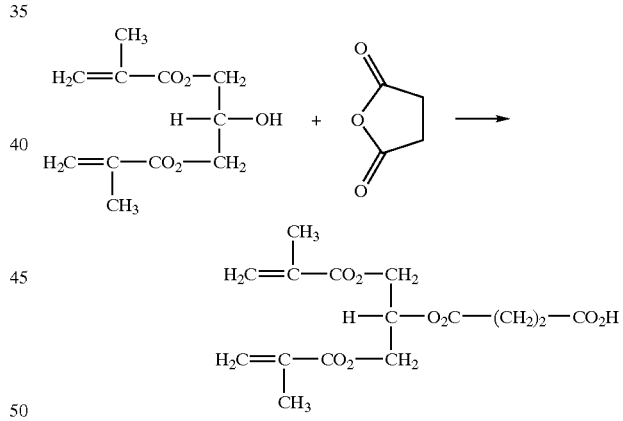

2. Synthesis of the Silane According to the Invention 19.8 g (0.08 mol) of 3-isocyanatopropyltriethoxysilane and, as a catalyst, 0.45 g (4.0 mol) of diazabicyclooctane (DABCO) are initially introduced, and 26.2 g (0.08 mol) of the carboxylic acid-modified dimethacrylate (from 1.) are added dropwise at 50° C. under a dry atmosphere. The reaction can be monitored via the decrease in the isocyanate band ($v_{(NCO)}=2273$ $cm^{-1}$) and via the formation and increase of the band associated with the resulting amido group in the IR spectrum. After the end of the addition and further stirring at 50° C. to complete the reaction, the desired product is obtained in the form of a clear, colorless liquid after customary working up.

| IR data: | $\nu_{(NH-amide)} \approx$ | 3324 cm$^{-1}$ |
| --- | --- | --- |
| | $\nu_{(C=O-amide)} \approx$ | 1657 cm$^{-1}$ |
| | $\nu_{(C=C-methacrylate)} \approx$ | 1655 cm$^{-1}$ |
| | $\nu_{(C=O-ester,methacrylate)} \approx$ | 1726 cm$^{-1}$ |

3. Hydrolysis and Condensation, Synthesis of the Polycondensate 8.64 g of water (+catalyst) are added to 80 mmol of the product from 2. in 80 ml of ethyl acetate for hydrolysis and condensation of the ethoxy groups, and stirring is carried out at room temperature. After the reaction is complete (detection by water titration), the solution, which is clear after working up, can be used, after addition of an initiator, for example for coating (with subsequent curing, i.e. polymerization of the methacrylate groups) any desired substrates.

4. Hydrolysis and Condensation, Synthesis of the Polycondensate 8.64 g of water (+catalyst) are added to 80 mmol of the product from 2. in 80 ml of ethyl acetate for hydrolysis and condensation of the ethoxy groups, and stirring is carried out at room temperature. After the reaction is complete (detection via water titration) and 27 mmol of dodecanediol dimethacrylate have been added, the solution, which is clear after working up, can be used, after addition of an initiator, for example for coating (with subsequent curing, i.e. polymerization of the methacrylate groups) any desired substrates.

Removal of the solvent gives a liquid resin (solvent-free application is thus possible) which, after addition of an initiator and curing (i.e. polymerization of the methacrylate groups), can be used, for example, for the production of moldings.

5. Curing, Polymerization of the Double Bonds

1% of Lucrin (photoinitiator) is dissolved in 10 g of the resin from 4. and added to a rod mold (2×2×25 mm$^3$). The methacrylate groups are subjected to a photoinitiated free radical polymerization reaction, the resin curing. For this purpose, exposure is effected on both sides using a spotlight. The modulus of elasticity and the breaking strength of the resulting rods are determined by means of the three-point bending test.

Modulus of elasticity=2.66 Gpa

Breaking strength=118 MPa

Excellent mechanical data thus result, and it is for this reason that the silanes according to the invention are very suitable, for example, for the production of matrix systems for dental composites.

What is claimed is:

1. A hydrolyzable and polymerizable organically modified silane of the general formula I

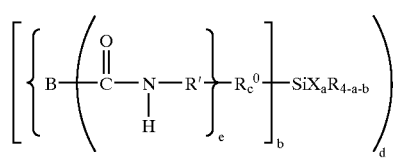

(I)

in which the radicals and indices have the following meaning:

B=straight-chain or branched substituted or unsubstituted organic radical having 2 to 50 carbon atoms comprising one or more acrylate and/or methacrylate groups, the —CO—NH— group in the formula I being bonded to a carbon atom of the radical B, and B containing no norbornene, bicyclo[2.2.2]oct-2-ene or 7-oxabicyclo [2.2.1]hept-2-ene group;

R=optionally substituted alkyl, alkenyl, aryl, alkylaryl or arylalkyl, each having 1 to 15 carbon atoms, it being possible for these radicals to contain oxygen and/or sulfur and/or nitrogen atoms;

R$^o$=optionally substituted alkylene, alkenylene, arylene, alkylenearylene or arylenealkylene, each having 1 to 15 carbon atoms, it being possible for these radicals to contain oxygen and/or sulfur and/or nitrogen atoms;

R'=optionally substituted alkylene, alkenylene, arylene, alkylenearylene or aryleneakylene, each having 1 to 15 carbon atoms, it being possible for these radicals to contain oxygen and/or sulfur and/or nitrogen atoms;

X=hydrogen, halogen, hydroxyl, alkoxy, acyloxy, alkylcarbonyl, alkoxycarbonyl or NR"$_2$, where R" is hydrogen, alkyl or aryl;

a=1, 2 or 3;

b=1, 2 or 3, and a+b=2, 3 or 4;

c=0 or 1;

d=1, 2, 3, 4, 5, 6, 7, 8, 9 or 10;

e=1.

2. The silane as claimed in claim 1, which has the general formula Ia

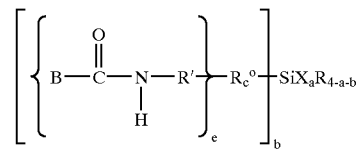

(Ia)

in which the radicals and indices are as defined in claim 1.

3. The silane as claimed in claim 1, which has the general formula Ic

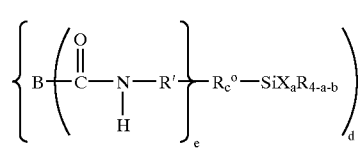

(Ic)

in which the radicals and indices are as defined in claim 1.

4. The silane as claimed in claim 1, which has the general formula Id

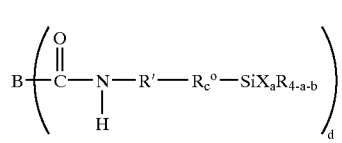

(Id)

in which the radicals and indices are as defined in claim 1.

5. The silane as claimed in claim 1, which has the general formula Ie

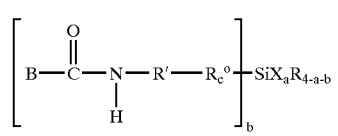

(Ie)

in which the radicals and indices are as defined in claim 1.

6. The silane as claimed in claim 1, which has the general formula Ig $$B-\overset{O}{\underset{H}{\overset{\|}{C}}}-N-R'-R_c^0-SiX_aR_{3-a-b} \quad (Ig)$$

in which the radicals and indices are as defined in claim 1.

7. The silane as claimed in claim 1, wherein, in the general formula I, the radicals and indices have the following meaning:

X=$(C_1-C_4)$-alkoxy or halogen;
R=$(C_1-C_4)$-alkyl;
R'=$(C_1-C_4)$-alkylene; and
B, $R^\circ$, a, b, c, d and e are as defined in claim 1.

8. The silane as claimed in claim 1, wherein the radical B is derived from acrylates and/or methacrylates of one or more of trimethylolpropane, glycerol, pentaerythritol, dipentaerythritol, $C_2-C_4$-alkanediols, polyethylene glycols, polypropylene glycols or optionally substituted and/or optionally alkoxylated bisphenol A.

9. A process for the preparation of a silane as claimed in claim 1, comprising reacting b×e moles of a compound $B(COOH)_d$ with d moles of a compound $[\{OCN-R'\}_e R^\circ_c]_b$ $SiX_aR_{4-a-b}$ under decarboxylating conditions, in which the radicals and indices are as defined in claim 1.

10. A method for the preparation of organically modified silica polycondensates or of organically modified silica heteropolycondensates comprising the hydrolytic condensation of one or more hydrolytically condensable compounds of silicon and optionally other elements from the group consisting of B, Al, P, Sn, Pb, the transition metals, the lanthanides and the actinides, and/or precondensates derived from the abovementioned compounds, optionally in the presence of a catalyst and/or of a solvent, by the action of water or of moisture, wherein from 1 to 100 mol %, based on monomeric compounds, of the hydrolytically condensable compounds are selected from silanes as claimed in claim 1 of the general formula I $$\left[\left[\left\{B\left(\overset{O}{\underset{H}{\overset{\|}{C}}}-N-R'\right)_e R_c^0\right\}_b SiX_aR_{4-a-b}\right)\right]_d \quad (I)$$

in which the radicals and indices are as defined in claim 1.

11. The method as claimed in claim 10, wherein the method comprises using compounds capable of free radical and/or ionic and/or covalent nucleophilic polymerization, optionally in precondensed form, as further hydrolytically condensable compounds.

12. The method as claimed in claim 10, wherein one or more initiators are added to the polycondensate and wherein the polycondensate is cured thermally and/or photochemically and/or by redox initiation.

13. The method as claimed in claim 10, wherein one or more components capable of free radical and/or ionic and/or covalent nucleophilic polymerization are added to the polycondensate before the curing.

14. A method for the preparation of polymers comprising one or more of free radical and/or ionic and/or covalent nucleophilic polymerization of one or more compounds containing C=C double bonds and optionally other compounds capable of one or more of free radical and/or ionic and/or covalent nucleophilic polymerization, by redox initiation and/or by the action of heat and/or of electromagnetic radiation and optionally in the presence of one or more initiators and/or of a solvent, wherein from 1 to 100 mol %, based on monomeric compounds, are selected from silanes as claimed in claim 1 of the formula I $$\left[\left[\left\{B\left(\overset{O}{\underset{H}{\overset{\|}{C}}}-N-R'\right)_e R_c^0\right\}_b SiX_aR_{4-a-b}\right)\right]_d \quad (I)$$

in which the radicals and indices are as defined in claim 1.

15. The method as claimed in claim 14, comprising the use of one or more spiroorthoesters, spiroorthocarbonates, bicyclic spiroorthoesters, methacryloylspiroorthoesters or mono- or oligoepoxides as cationically polymerizable compounds.

16. The method as claimed in claim 14, wherein the polymer is hydrolytically condensed, optionally in the presence of further hydrolytically condensable compounds of silicon and optionally other elements from the group consisting of B, Al, P, Sn, Pb, the transition metals, the lanthanides and the actinides, and/or precondensates derived from the abovementioned compounds, by the action of water or moisture, optionally in the presence of a catalyst and/or of a solvent.

17. A method for the preparation of one or more products selected from the group consisting of polycondensates, heteropolycondensates, polymers, bulk materials, composites, adhesives, casting and sealing compounds, coating materials, coatings, abrasives, adhesion promoters, binders, fillers, fibers, films, (contact) lenses and dental restoration materials, comprising using a silane as claimed in claim 1 to form said one or more products.

18. A silane as claimed in claim 1, having the structure

19. The silane as claimed in claim 7, wherein, in the general formula I, the radicals and indices have the following meaning:

X=methoxy, ethoxy, or Cl;
R=methyl or ethyl; and
R'=methylene, ethylene or propylene.

* * * * *